United States Patent [19]

Allen et al.

[11] Patent Number: 5,106,385

[45] Date of Patent: Apr. 21, 1992

[54] ADJUSTABLE DIAPER AND METHOD OF FOLDING SAME

[75] Inventors: Linda S. Allen; Wendy A. Harrison, both of Greeley, Colo.

[73] Assignee: Aware Diaper, Inc., Greeley, Colo.

[21] Appl. No.: 571,211

[22] Filed: Aug. 23, 1990

[51] Int. Cl.⁵ .................. A61F 13/15; A61F 13/20
[52] U.S. Cl. ............................ 604/391; 604/385.1
[58] Field of Search ............... 604/358, 385.1, 385.2, 604/386, 389, 391, 394, 400

[56] References Cited

U.S. PATENT DOCUMENTS

| | | | |
|---|---|---|---|
| 3,150,664 | 9/1964 | Noel | 604/391 |
| 3,618,608 | 11/1971 | Brink | 128/287 |
| 4,402,690 | 9/1983 | Redfern | 604/391 |
| 4,410,327 | 10/1983 | Baggaley | 604/391 |
| 4,475,912 | 10/1984 | Coates | 604/391 X |
| 4,568,342 | 2/1986 | Davis | 604/391 |
| 4,597,759 | 7/1986 | Johnson | 604/389 X |
| 4,680,030 | 7/1987 | Coates et al. | 604/391 |
| 4,681,581 | 7/1987 | Coates | 604/391 |
| 4,704,117 | 11/1987 | Mitchell | 604/391 |
| 4,728,326 | 3/1988 | Gilles | 604/391 |
| 4,753,646 | 6/1988 | Enloe | 604/385.2 |
| 4,773,906 | 9/1988 | Krushel | 604/391 |
| 4,801,298 | 1/1989 | Sorenson et al. | 604/386 X |

FOREIGN PATENT DOCUMENTS 8303754 11/1983 World Int. Prop. O. ......... 604/391

Primary Examiner—David Isabella
Assistant Examiner—Elizabeth M. Burke
Attorney, Agent, or Firm—John E. Reilly

[57] ABSTRACT

A diaper has an elongated panel made of a flexible absorbent material with laterally spaced fasteners in back-to-back relation at one end of the panel and a complementary fastener at the other end for interchangeable releasable attachment to selected ones of the laterally spaced fasteners according to the direction of folding of the one end to reduce the effective size of the diaper. An extension panel is provided to increase the effective size of the diaper and which extension panel is releasably secured to the laterally spaced fasteners.

9 Claims, 2 Drawing Sheets

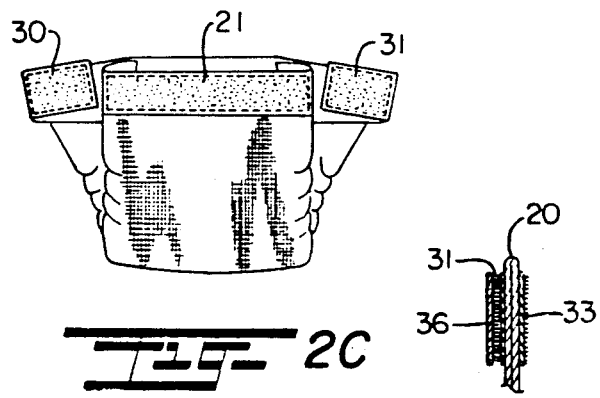
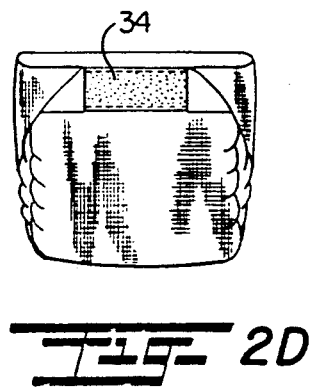
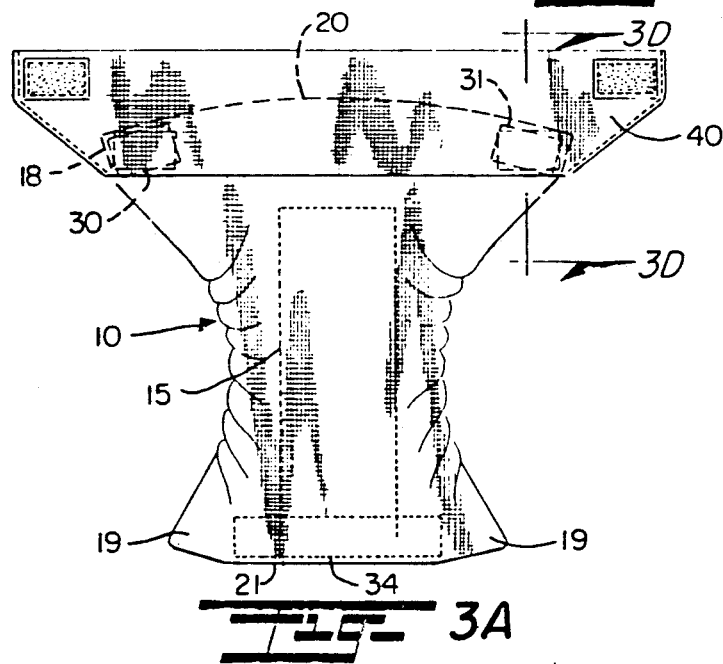
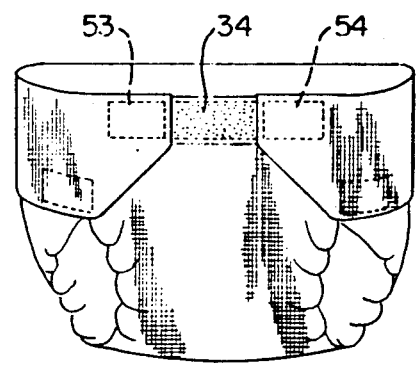
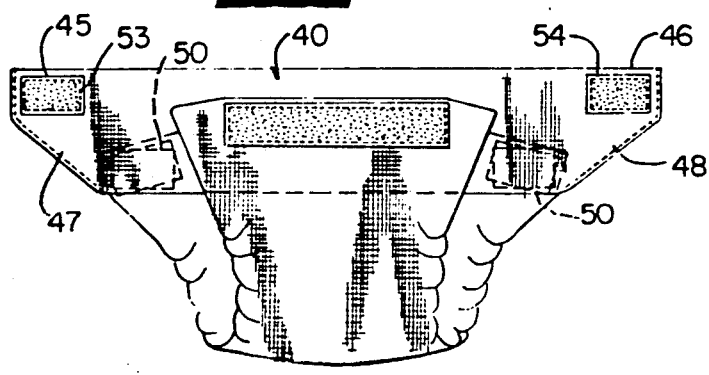
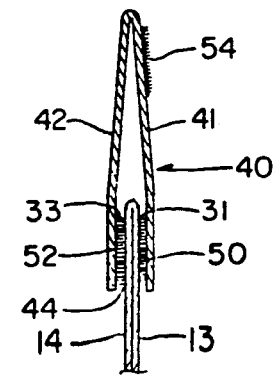

ADJUSTABLE DIAPER AND METHOD OF FOLDING SAME

This invention relates to diapers; and more particularly relates to a novel and improved reusable diaper and method of folding same which is conformable for fitting and use for different sized persons.

BACKGROUND AND FIELD OF THE INVENTION

Cloth or fabric diapers are becoming increasingly popular, since they are reusable and avoid many of the problems associated with plastic or disposable diapers. Cloth diapers are more expensive to manufacture, and a particular problem confronted by the consumer is the cost of purchasing different-sized diapers for the growing infant. It is therefore desirable to provide for a single diaper size together with fastening system which will enable the diaper to be adjusted in size and securely but easily fastened to conform to the size and shape of the infant.

So-called hook and pile fasteners customarily sold under the trademark "VELCRO®" are in widespread use on reusable diapers and such fastening systems do afford some degree of adjustability particularly in the waist size of the diaper. Representative patents are U.S. Pat. Nos. 4,680,030 and 4,681,581 to F. V. Coates, 4,568,342 to C. W. Davis, 4,801,298 to W. K. J. Sorenson et al and 4,410,327 to N. E. Baggaley. Although these patents are of interest from the standpoint of affording greater degree of adjustability in a diaper, there is a definite need for a diaper construction which can be varied over a wide range in sizes and enables secure attachment and fitting in each size.

SUMMARY OF THE INVENTION

It is therefore an object of the present invention to provide for a novel and improved control diaper and method of folding same which obviates different sized diapers and is highly efficient and reliable in use.

It is another object of the present invention to provide in a diaper for a novel and improved fastening system which in combination with the diaper makes it readily conformable for fitting different sized individuals; and specifically wherein the diaper is capable of being folded to more closely fit and conform to an infant beginning with the newborn and up to advanced stages of growth.

It is a further object of the present invention to provide for a method of folding a diaper and fastening system which will enable adjustment in width and in length of the diaper to conform to different sized infants but at the same time avoids any undue bunching or folding of the diaper material.

It is an additional object of the present invention to provide for a reusable diaper having a novel and improved fastening system which will withstand repeated use and laundering; and further wherein an extension panel is provided for use in combination with the diaper to accommodate larger sized infants and is economical to manufacture and simple to use.

In accordance with the present invention, a preferred form of diaper is composed of a flexible absorbent material and which comprises an elongated panel having inner and outer surfaces, wing portions extending laterally from opposite sides of the panel, a first pair of laterally spaced fastener means on the inner surface at one of the opposite ends of the panel, a second pair of laterally spaced fastener means on the outer surface at the one end of the panel, and complementary fastening means on the outer surface at the opposite end of the panel for interchangable releasable attachment to either one of the first or second pair of laterally spaced fastener means.

In the preferred form, the fastener means are Velcro tabs having the hook portions making up the first and second pair of fastener means and the pile portion defining the complementary fastener means and extending across the substantial width of the panel. In order to expand or substantially increase the size of the diaper, an extension panel in the form of an envelope has a lower open end with laterally spaced fastener means which are engageable with the first and second pairs of laterally spaced fastener means on the elongated panel, and the upper divergent end of the extension panel includes fastener means engageable with the complementary fastener means at the opposite free end of the elongated panel.

In the preferred method of folding the diaper, the effective length of the diaper is established by folding the one end inwardly and downwardly such that the second pair of fastener means faces inwardly, then wrapping the one end of the panel around the opposite end to align the second pair of fastener means with the complementary fastener means, followed by attaching the second fastener means to the complementary fastener means to establish the desired waist size of the diaper.

In order to further reduce the size of the diaper, the wing portions are first laterally folded at the one end of the panel over the outer surface, the one end is then folded inwardly and downwardly so that the first pair of fastener means face inwardly, then folding the panel in half to bring the opposite end into a juxtaposed position to the one end of the panel followed by wrapping the one end around the opposite end and attaching the first pair of fastener means to the complementary fastener means to establish the desired waist size.

Other objects, advantages and features of the present invention will become more readily appreciated and understood when taken together with the following detailed description in conjunction with the accompanying drawings, in which:

BRIEF DESCRIPTION OF THE DRAWINGS

FIGS. 2A-2E illustrate the preferred form of diaper in conjunction with a modified form of folding same to further reduce the size from that illustrated in FIGS. 1A to 1D, and FIG. 2E being a cross-sectional view taken about lines 2E-2E of FIG. 2C; and FIGS. 3A to 3D illustrate the preferred form of diaper used in association with an extension panel to increase the size of the diaper, and wherein FIG. 3D is a cross-sectional view taken about lines 3D-3D of FIG. 3A.

DETAILED DESCRIPTION OF THE PREFERRED EMBODIMENT

Figure 1A:
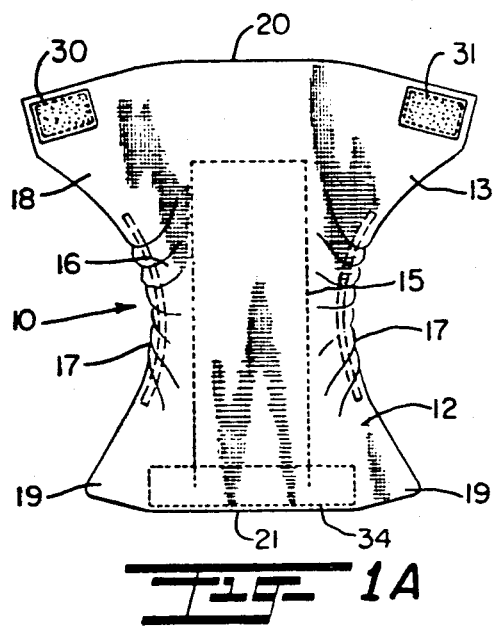
FIGS. 1A to 1D illustrate a preferred form of diaper and method of folding to reduce the effective size of the diaper from that illustrated in FIG. 1A.

Referring in more detail to the drawings, a preferred form of diaper 10 is illustrated in FIGS. 1A-1D and comprises an elongated panel 12 of moisture absorbent, flexible fabric material including an inner surface 13 which makes contact with the skin and an outer surface 14 which is coextensive with the inner surface. In accordance with conventional practice, the diaper is comprised of layers of a fabric material which are seamed or otherwise united together and including an intermediate moisture absorbent layer 15 as illustrated in dotted form in FIGS. 1A and 1B. Typically, the entire panel is formed with a relatively narrow crotch or central area 16 through the utilization of elastic sections 17 on opposite sides of the panel to gather the material along the central area 16. The panel diverges away from the central area 16 into wing portions 18 and 19 which terminate, respectively, in opposite ends 20 and 21 of the panel. The foregoing is given merely by way of illustration of a representative form of diaper construction and as a setting for the novel features of the present invention.

In accordance with the present invention, a first pair of fastener tabs 30 and 31 are disposed in laterally spaced relation to one another at the one end 20 of the panel 12 and on the inner surface of the wing portions 18. A second pair of fastener tabs 32 and 33 is disposed in back-to-back relation to the tabs 30 and 31 on the outer surface of the wing portions so as to face in a direction away from that of the tabs 30 and 31. Each of the tabs 30 to 33 is correspondingly of square or generally rectangular configuration and may be directly secured by sewing through the thickness of the panel.

A complementary fastener in the form of an elongated bar 34 is disposed on the outer surface at the opposite end 21 of the panel so as to extend in a lateral direction intermediately between the wing portions 19. The fastener 34 is complementary to the fastener straps 30 to 33 in the sense that it will facilitate releasable connection of either pair of tabs 30, 31 or 32, 33 when pressed against the fastener 34. To this end, the fasteners 30 to 34 as described are preferably of a hook and loop or pile type construction sold under the trademark "VELCRO" with the tabs 30 to 33 being in the form of hook portions and the fastener bar 34 being the loop portion. In this way, any exposed portion of the front bar 34 will be smooth, as opposed to the relatively rough surface of the hook portions, and the loop or pile surface is not as susceptible to collecting lint as the hook portions. To the extent that any of the portions are exposed, they can be covered in a conventional manner by utilization of tab covers so as to protect them during laundering. As will become more readily appreciated from the following description of different methods of folding the diaper, there is minimal exposure of the hook portions in the different folded or reduced size configurations.

FIG. 1 illustrates a diaper in an unfolded position in which it can be secured in the usual fashion by laying the infant on the inner surface of the panel 12 so that the one end 20 is beneath the hips and back of the infant, and the opposite end 21 can be lifted upwardly between the legs and over the tummy or waist portion of the infant with the bar 34 facing forwardly. The tabs 30 and 31 are then wrapped around the front wing portions 19 into overlapping relation to the bar 34 and pressed into position against the bar with the diaper in snug-fitting relation around the waist of the infant.

An effective method of folding is followed in cases where it is necessary to reduce the effective length of the diaper for smaller-sized infants. As illustrated in FIG. 1B, the one end 20 is folded inwardly and downwardly so that the outside tabs 32 and 33 are then facing inwardly and the inside tabs 30 and 31 are facing in an outward direction against the inner surface of the panel. When the infant is placed on the diaper, the opposite end 21 is again lifted between the legs and over the tummy portion as shown in FIG. 1C and the one end then wrapped around the opposite end to align the fastener tabs 32 and 33 with the bar 34 and then attached to the bar so as to establish the desired waist size of the diaper, as illustrated in FIG. 1D.

Figure 1B:
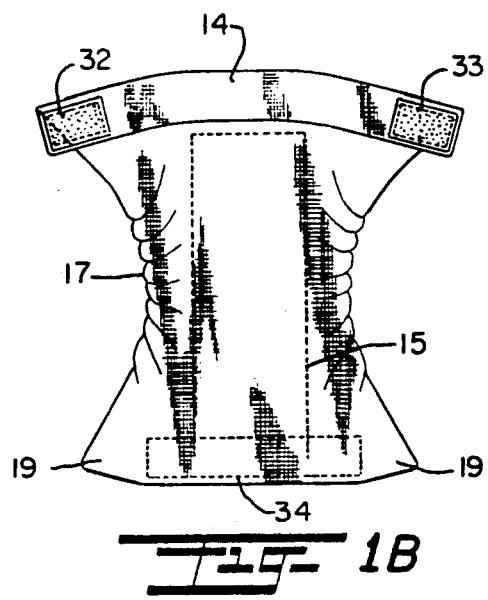
Figure 1C:
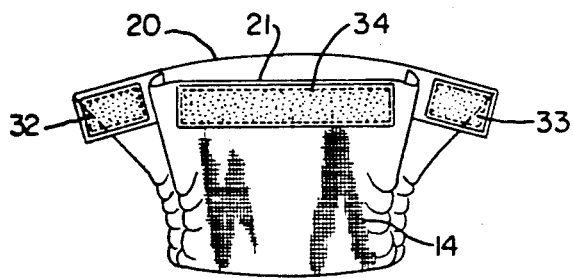
Figure 1D:
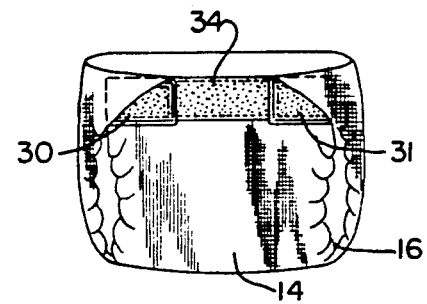
Figure 2A:
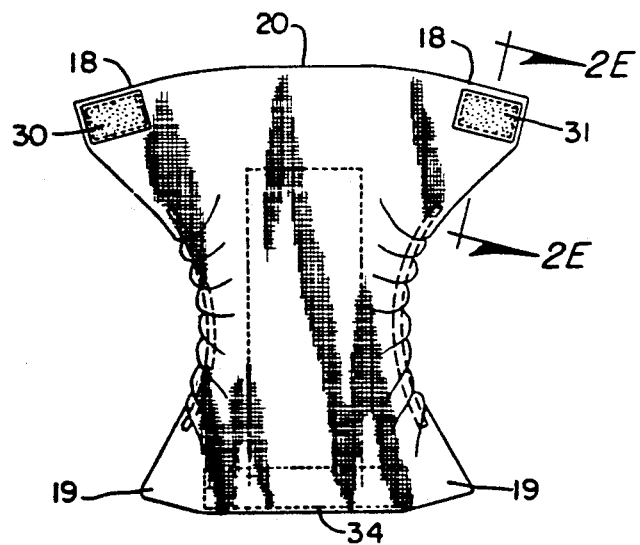
Figure 2B:
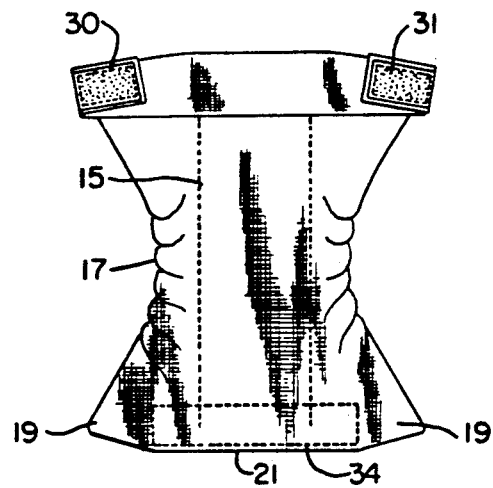

FIGS. 2A to 2E illustrate an alternate method of folding a diaper as illustrated in FIG. 1A in which both the effective length and waist size are substantially reduced for still smaller sized infants than those for which the folding method of 1B to 1D is intended. To this end, the wing portions 18 are first laterally folded at the one end 20 in a rearward direction over the outer surface 14, after which the one end 20 is then folded inwardly and downwardly whereby the first pair of fastener tabs 30 and 31 face inwardly, as shown in FIG. 2B. As further shown in FIG. 2C, after placing the infant on the folded diaper, the opposite end 21 is positioned over the tummy or waist portion, after which the tabs 30 and 31 are wrapped around the opposite end 21 into overlapping relation to the bar 34 whereupon the tabs 30 and 31 can then be attached to the bar.

FIGS. 3A to 3D illustrate the utilization of the preferred form of diaper 10 in combination with an extension panel 40 in order to substantially increase the effective size of the diaper without modifying its construction. For this purpose, the diaper 10 is constructed in the same manner as illustrated in FIGS. 1A and 2A and like parts to those illustrated in FIGS. 1A and 2A are correspondingly enumerated. The extension panel 40 is composed of a cloth or fabric material which is doubled over to form an inner layer 41 and outer layer 42 with a lower open end 44. Preferably, the extension panel 40 diverges in an upward direction away from the lower open end to terminate in extension wing portions 45 and 46 at uppermost corners of the extension panel. The inner and outer layers 41 and 42 are stitched together along opposite lateral sides as designated at 47 and 48 so as to define a generally envelope-shaped construction and where the lower end 44 is of a width to permit insertion of the one end 20 of the diaper 10.

A pair of laterally spaced fastener tabs 50 are provided on the interior surface of the inner layer 41 so as to be aligned in facing relation to the first pair of tabs 30 and 31 at the one end 20 of the diaper; and a second pair of laterally spaced fastener tabs 52 are disposed on the interior surface of the outer layer 42 in alignment with the second pair of fastener tabs 32 and 33 on the outer surface of the diaper 10. The fastener tabs 50 and 52 are complementary to the fastener tabs 30-33 or, in other words, are made up of a loop-type fastening material which will interengage with the hook-type tabs 30-33 so as to firmly but releasably secure the extension panel 40 to the one end of the diaper. Extension fastener tabs 53 and 54 are disposed on the inner surface of each wing portion 45 and 46, respectively, so that the extension panel may be wrapped around the waist with the tabs brought into alignment and in overlapping relation to the complementary fastener bar 34 at the opposite end of the diaper in the manner shown in FIG. 3C. The tabs 53 and 54 are then firmly pressed into engagement with the bar to secure the diaper in place.

From the foregoing, it will be appreciated that the extension panel 40 can be readily separated from the diaper 10 for laundering purposes and is then easily reattachable for subsequent use. Of course, the extension panel 40 may be dimensioned to be of various sizes and configurations. Moreover, while preferred and alternate forms of diaper constructions have been characterized as being fabricated of a cloth material, the fastening system as described is readily adaptable for use with other materials. In this relation, the fastener tabs as shown afford a wide range of adjustability in assuming different folded configurations as well as to facilitate attachment of an extension panel as described. In the different forms of invention as described, the wing portions 19 extend laterally some distance beyond the bar 34 to prevent direct contact between the hook-type fastener tabs and the baby's skin in the event that the tabs should extend beyond the end of the bar 34 when fastened.

Accordingly, while preferred and modified forms of diaper constructions and methods of folding have been hereinset forth and described, it is to be understood that various modifications and changes may be made in the specific construction and arrangement of parts as well as their method of folding without departing from the spirit and scope of the present invention as defined by the appended claims and reasonable equivalents thereof.

We claim:

1. A diaper composed of a flexible absorbent material comprising:
    an elongated panel defining a length and a width and having an inner surface and a coextensive outer surface;
    wing portions extending laterally outward at opposite ends of said panel;
    a first pair of laterally spaced fastener means on said inner surface at one of said ends;
    a second pair of laterally spaced fastener means on said outer surface at said one end of said panel; and
    complementary fastening means on said outer surface at said opposite end being complementary to each of said first pair and said second pair of said laterally spaced fastener means for interchangeable releasable attachment to one of said first and said second pair of laterally spaced fastener means.

2. A diaper according to claim 1, said complementary fastening means extending laterally across the width of said opposite end.

3. A diaper according to claim 1, said first and second pair of laterally spaced fastening means disposed in back-to-back relation to one another on said wing portions at said one end, and said complementary fastening means disposed intermediately between said wing portions at said opposite end of said panel.

4. A diaper composed of a flexible absorbent material comprising:
    an elongated panel defining a length and a width and having an inner surface and a coextensive outer surface;
    wing portions extending laterally outward at opposite ends of said panel;
    a first pair of laterally spaced fastener means on said inner surface at one of said ends;
    a second pair of laterally spaced fastener means on said outer surface at said one end of said panel;
    complementary fastening means on said outer surface at said opposite end for interchangeable releasable attachment to one of said first and said second pair of laterally spaced fastener means; and
    an extension panel forming an envelope having a lower open end corresponding in width to the width of said elongated panel, and laterally spaced fastener means at said open end engageable with said first and second pair of laterally spaced fastener means on said elongated panel.

5. A diaper according to claim 4, said extension panel diverging upwardly from said elongated panel and including a third pair of laterally spaced fastener means at opposite sides of said extension panel on an inner surface of said extension panel engageable with said complementary fastener means when said opposite sides of said extension panel are disposed in overlapping relation to said complementary fastener means.

6. A method of folding a diaper, said diaper formed of an elongated panel of flexible absorbent material including an inner surface and an outer surface, a first pair of fastener tabs at one end of said inner surface, a second pair of fastener tabs on said outer surface and at said one end of said panel, and complementary fastener means on said outer surface at an end opposite to said one end, the method of folding said diaper comprising the steps of:
    (a) folding said one end inwardly and downwardly to establish a predetermined effective length of said diaper with said second pair of fastener tabs facing inwardly;
    (b) wrapping said one end around said opposite end to align said second pair of fastener tabs with said complementary fastener means; and
    (c) attaching said second pair of fastener tabs to said complementary fastener means to establish a desired waist size of said diaper.

7. In a method according to claim 6, wherein said first and second pairs of fastener tabs are disposed in back-to-back relation to one another on the diaper, and step (a) includes positioning said first pair of fastener tabs to face outwardly against the inner surface of said panel.

8. A method of folding a diaper, said diaper being formed of an elongated panel of absorbent material including an inner surface and an outer surface, wing portions diverging in lateral directions away from opposite ends of said panel, a first pair of laterally spaced fastener tabs on said inner surface at one end of said panel, a second pair of laterally spaced fastener tabs on said outer surface at said one end of said panel, and complementary fastener means on said outer surface at said opposite end of said panel, the method of folding comprising the steps of:
    (a) laterally folding said wing portions at said one end;
    (b) folding said one end inwardly and downwardly;
    (c) folding said panel in half to bring said opposite end into juxtaposed position to said one end;
    (d) wrapping said one end around said opposite end to align said one of said first and second pairs of fastener tabs in overlapping relation to said complementary fastener means; and
    (e) attaching said one of said first and second pairs of fastener tabs to said complementary fastener means to establish the desired waist size.

9. A method of folding a diaper, said diaper being formed of an elongated panel of absorbent material including an inner surface and an outer surface, wing portions diverging in lateral directions away from opposite ends of said panel, a first pair of laterally spaced fastener tabs on said inner surface at one end of said panel, a second pair of laterally spaced fastener tabs on said outer surface at said one end of said panel, and complementary fastener means on said outer surface at said opposite end of said panel, the method of folding comprising the steps of:

(a) laterally folding said wing portion at said one end over said outer surface of said panel;

(b) folding said one end inwardly and downwardly whereby said first pair of fastener means face inwardly;

(c) folding said panel in half to bring said opposite end into juxtaposed position to said one end;

(d) wrapping said one end around said opposite end to align said first pair of fastener tabs in overlapping relation to said complementary fastener means; and (e) attaching said first pair of fastener tabs to said complementary fastener means to establish a desired waist size.

* * * * *